(12) United States Patent
Siegert et al.

(10) Patent No.: US 8,378,144 B2
(45) Date of Patent: Feb. 19, 2013

(54) PROCESS FOR PREPARING POLYOXYMETHYLENE HOMOPOLYMERS OR COPOLYMERS BY HOMOPOLYMERIZATION OR COPOLYMERIZATION OF TRIOXANE, STARTING FROM METHANOL

(75) Inventors: Markus Siegert, Heidelberg (DE);
Tobias Kortekamp, Mannheim (DE);
Eckhard Stroefer, Mannheim (DE);
Christoph Sigwart, Weinheim (DE);
Neven Lang, Mannheim (DE)

(73) Assignee: BASF SE (DE)

( * ) Notice: Subject to any disclaimer, the term of this patent is extended or adjusted under 35 U.S.C. 154(b) by 435 days.

(21) Appl. No.: 12/747,742

(22) PCT Filed: Dec. 11, 2008

(86) PCT No.: PCT/EP2008/067286
§ 371 (c)(1),
(2), (4) Date: Jun. 11, 2010

(87) PCT Pub. No.: WO2009/077415
PCT Pub. Date: Jun. 25, 2009

(65) Prior Publication Data
US 2010/0280195 A1    Nov. 4, 2010

(30) Foreign Application Priority Data
Dec. 19, 2007  (EP) .................................... 07150113

(51) Int. Cl.
*C07C 213/00*  (2006.01)

(52) U.S. Cl. ........ 564/505; 568/620; 568/679; 568/623; 568/624; 528/403; 528/249; 526/67

(58) Field of Classification Search ............... 564/505; 568/620, 679, 624, 625, 623; 528/403, 249; 526/67
See application file for complete search history.

(56) References Cited

FOREIGN PATENT DOCUMENTS

| | | |
|---|---|---|
| EP | 128739 | 12/1984 |
| EP | 129369 | 12/1984 |
| WO | WO-2006/042759 | 4/2006 |
| WO | WO-2007/023187 | 3/2007 |
| WO | WO-2008/090169 | 7/2008 |
| WO | WO-2009/047109 | 4/2009 |

OTHER PUBLICATIONS

Translation of International Preliminary Report on Patentability for PCT/EP2008/067286, dated Jun. 19, 2010.

*Primary Examiner* — Shane Fang
(74) *Attorney, Agent, or Firm* — Novak Druce Connolly Bove + Quigg LLP

(57) ABSTRACT

A process for preparing polyoxymethylene homopolymers or copolymers (7) by homopolymerization or copolymerization of trioxane, starting from methanol (1), in which
methanol (1) is oxidized in a first reactor in a first production plant (A) to give an aqueous formaldehyde-comprising stream (2) which
is fed to a second production plant (B) in which pure trioxane (6) is obtained and removal of low boilers (5) by distillation is carried out and
the pure trioxane (6) is fed to a third production plant (C) in which it is homopolymerized or copolymerized to form polyoxymethylene homopolymers or copolymers (7), wherein the low boiler stream (5) from the low boiler removal column (K 2) is recycled to the feed stream into the first reactor in the first production plant (A), is proposed.

2 Claims, 2 Drawing Sheets

Figure 1:
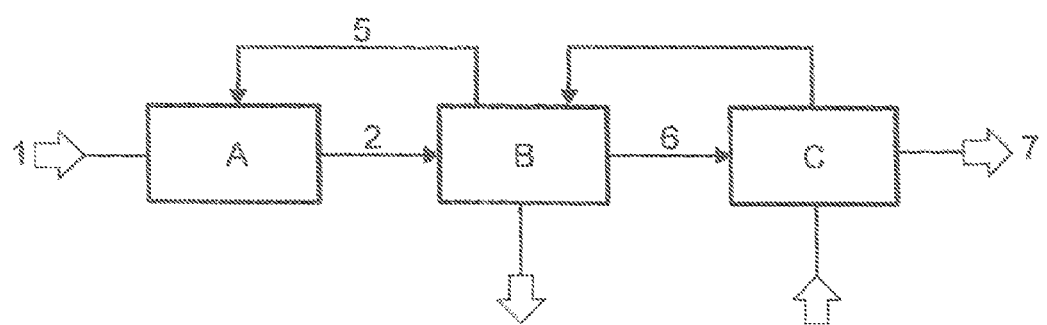

PROCESS FOR PREPARING POLYOXYMETHYLENE HOMOPOLYMERS OR COPOLYMERS BY HOMOPOLYMERIZATION OR COPOLYMERIZATION OF TRIOXANE, STARTING FROM METHANOL

CROSS REFERENCE TO RELATED APPLICATIONS

This application is a national stage application under 35 U.S.C. §371 of PCT/EP2008/067286, filed Dec. 11, 2008, which claims benefit to European application 07150113.4, filed Dec. 19, 2007, the entire disclosures of which are hereby incorporated by reference.

DESCRIPTION

The invention relates to a process for preparing polyoxymethylene homopolymers or copolymers by homopolymerization or copolymerization of trioxane, starting from methanol.

Trioxane is obtained predominantly by trimerization of formaldehyde from aqueous formaldehyde solutions by homogeneous or heterogeneous catalysis in the presence of acid catalysts. A problem here is that formaldehyde tends to precipitate as solid with formation of paraformaldehyde, with the temperature at which the solid begins to precipitate decreasing with increasing formaldehyde content of an aqueous solution. As an approximation, at least for formaldehyde concentrations in the range from 30 to 70% by weight, aqueous formaldehyde solutions have to be heated to a temperature which is about 10° C. higher than the concentration of formaldehyde in % by weight in order to avoid precipitation of a solid. Thus, a 50% strength aqueous formaldehyde solution has to be heated to about 60-70° C. and a 60% strength formaldehyde solution has to be heated to about 70-80° C. in order to keep the formaldehyde in solution. Formaldehyde is in turn predominantly obtained by oxidation of methanol.

The trioxane obtained by trimerization of formaldehyde is, if appropriate together with further monomers, predominantly used as monomer for preparing polyoxymethylene homopolymers or copolymers.

Polymerization-grade trioxane has to meet particular specifications and will hereinafter be referred to as pure trioxane. This is a stream having a minimum content of 97.5% by weight of trioxane or even 99% by weight of trioxane or 99.5% by weight of trioxane. A stream having a minimum content of 99.9% by weight of trioxane can be referred to as high-purity trioxane.

The production of pure trioxane by concentration of the reaction mixture from the trimerization of formaldehyde is made difficult in process engineering terms by trioxane, formaldehyde and water forming a ternary azeotrope which at a pressure of 1 bar has the composition 69.5% by weight of trioxane, 5.4% by weight of formaldehyde and 25.1% by weight of water and whose composition is strongly pressure-dependent.

Pure trioxane is therefore preferably obtained by pressure swing rectification as is described, for example, in the earlier-priority DE-A 07 101 198, which is not a prior publication, or EP 07 118 103.6. This requires elevated pressures and corresponding temperatures at which the desired product trioxane decomposes to form low boilers, i.e. substances having a boiling point lower than the boiling point of trioxane. Low boilers are in the present case, in particular, methyl formate, methylal, bis(methoxymethyl) ether and methanol.

The decomposition of the desired product trioxane leads to yield losses which impair the economics of the process.

It was therefore an object of the invention to provide a technically simple process for preparing pure trioxane which is subsequently polymerized in a polymer plant to give polyoxymethylene homopolymers or copolymers, starting from methanol, which minimizes the above-described yield losses.

This object is achieved by a process for preparing polyoxymethylene homopolymers or copolymers by homopolymerization or copolymerization of trioxane, starting from methanol, in which
methanol is oxidized in a first reactor in a first production plant to give an aqueous formaldehyde-comprising stream which
is fed to a second production plant in which
the formaldehyde is trimerized in the presence of an acid catalyst in a second reactor to form trioxane and from which a trioxane/formaldehyde/water mixture is taken off,
the trioxane/formaldehyde/water mixture is fractionally distilled in a first column to give crude trioxane as overhead stream
and the overhead stream is condensed in a condenser at the top of the column to give a condensate, a substream of the condensate is returned to the first column and the remaining substream is passed to further work-up in one or more further process stages to give pure trioxane, with one of these further process stages comprising removal of low boilers selected from the group consisting of methyl formate, methylal, bis(methoxymethyl) ether and methanol by distillation in a low boiler removal column, and
the pure trioxane is fed to a third production plant in which it is homopolymerized or copolymerized to form polyoxymethylene homopolymers or copolymers, wherein the low boiler stream from the low boiler removal column is recycled to the feed stream into the first reactor in the first production plant.

The preparation of formaldehyde by oxidation of methanol in a first reactor in a first production plant is known per se. This gives an aqueous formaldehyde-comprising stream which is fed to a second production plant in which the formaldehyde is trimerized in the presence of an acid catalyst in a second reactor to form trioxane.

The trioxane/formaldehyde/water mixture obtained here is fractionally distilled in a first column to give crude trioxane as overhead stream.

The trioxane/formaldehyde/water mixture which is fed to the first column generally comprises from 40 to 80% by weight of formaldehyde, from 20 to 59% by weight of water and from 1.0 to 30% by weight of trioxane.

The overhead stream from the first column, referred to as crude trioxane, generally comprises more than 60% by weight, preferably more than 63% by weight, particularly preferably more than 65% by weight, of trioxane. For example, the crude trioxane overhead stream from the first column has the following composition: from 3 to 20% by weight of formaldehyde, from 10 to 30% by weight of water and from 60 to 75% by weight of trioxane.

The overhead stream from the first distillation column is condensed in a condenser at the top of the column to give a condensate, a substream of the condensate is returned as runback to the first column and the remaining substream is passed to further work-up in one or more further process stages to give pure trioxane.

For the present purposes, pure trioxane is a stream having a minimum content of 97.5% by weight of trioxane or even 99% by weight of trioxane or even 99.5% by weight of trioxane. One of these further process stages for the work-up of crude trioxane to give pure trioxane comprises a removal of low boilers by distillation.

Usual low boilers which can be formed in the trioxane synthesis and the subsequent fractional distillation are methyl formate, methylal, bis(methoxymethyl) ether, methanol, formic acid and also further hemiacetals and full acetals.

The low boilers are preferably separated off via the top of a low boiler removal column which is generally operated at a pressure of from 0.1 to 5 bar, preferably at a pressure of from 1.0 to 2.5 bar. The stream fed to the low boiler removal column can generally comprise up to 15% by weight of low boilers.

In general, the low boiler removal column has at least 2 theoretical plates, preferably from 15 to 50 theoretical plates. In general, the stripping section of this column comprises from 25 to 90%, preferably from 50 to 75%, of the theoretical plates of this column.

In general, less than 5% by weight, preferably less than 2.5% by weight, particularly preferably less than 1.5% by weight, of the components having boiling points lower than that of trioxane remain in the bottom output from the low boiler removal column.

The pure trioxane is fed to a third production plant in which it is homopolymerized or copolymerized to form polyoxymethylene homopolymers or copolymers.

According to the invention, the low boiler stream which is taken off as overhead stream from the low boiler removal column is recycled to the feed stream to the first reactor in the first production plant.

The low boiler stream preferably comprises the following main components:

methanol up to 50% by weight, methyl formate up to 40% by weight, methylal up to 30% by weight and trioxane less than 10% by weight.

It is advantageous not only to couple the production plants A and B, i.e. the formaldehyde production plant and the trioxane production plant, but also to couple the trioxane production plant to the production plant C, viz. the plant for the polymerization of pure trioxane to form polyoxymethylene homopolymers or copolymers.

Polyoxymethylene homopolymers or copolymers (POM) quite generally have at least 50 mol % of recurring —$CH_2O$— units in the main polymer chain. Polyoxymethylene copolymers are preferred, in particular those which have, in addition to the recurring —$CH_2O$— units, up to 50 mol %, preferably from 0.01 to 20 mol %, in particular from 0.1 to 10 mol % and very particularly preferably from 0.5 to 6 mol %, of recurring units

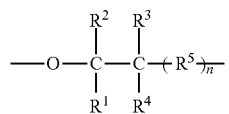

where $R^1$ to $R^4$ are each, independently of one another, a hydrogen atom, a $C_1$-$C_4$-alkyl group or a halogen-substituted alkyl group having from 1 to 4 carbon atoms and $R^5$ is a —$CH_2$— group, a —$CH_2O$— group, a $C_1$-$C_4$-alkyl- or $C_1$-$C_4$-haloalkyl-substituted methylene group or a corresponding oxymethylene group and n is from 0 to 3. These groups can advantageously be introduced into the copolymers by ring opening of cyclic ethers. Preferred cyclic ethers are those of the formula

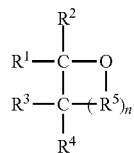

where $R^1$ to $R^5$ and n are as defined above. Purely by way of example, mention may be made of ethylene oxide, 1,2-propylene oxide, 1,2-butylene oxide, 1,3-butylene oxide, 1,3-dioxane, 1,3-dioxolane and 1,3-dioxepane (=butanediol formal, BUFO) as cyclic ethers and also of linear oligoformals or polyformals such as polydioxolane or polydioxepane as comonomers.

Further suitable polymers are oxymethylene terpolymers which are prepared, for example, by reaction of trioxane and one of the above-described cyclic ethers with a third monomer, preferably a bifunctional compound of the formulae

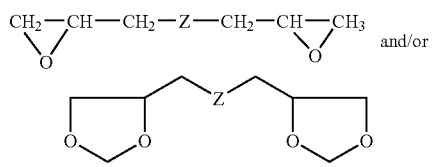

where Z is a chemical bond, —O—, —ORO— (R=$C_1$-$C_8$-alkylene or $C_3$-$C_8$-cycloalkylene).

Preferred monomers of this type are ethylene diglycide, diglycidyl ether and diethers derived from glycidyls and formaldehyde, dioxane or trioxane in a molar ratio of 2:1 and also diethers derived from 2 mol of glycidyl compound and 1 mol of an aliphatic diol having from 2 to 8 carbon atoms, for example the diglycidyl ethers of ethylene glycol, 1,4-butanediol, 1,3-butanediol, cyclobutane-1,3-diol, 1,2-propanediol and cyclohexane-1,4-diol, to name only a few examples.

End-group-stabilized polyoxymethylene polymers which have predominantly C—C or —O—$CH_3$ bonds at the ends of the chain are particularly preferred.

The preferred polyoxymethylene copolymers have melting points of at least 150° C. and molecular weights (weight average) $M_w$ in the range from 5000 to 300 000 g/mol, preferably from 7000 to 250 000 g/mol. Particular preference is given to POM copolymers having a polydispersity ($M_w/M_n$) of from 2 to 15, preferably from 2.5 to 12, particularly preferably from 3 to 9. The measurements are generally carried out by gel permeation chromatography (GPC)-SEC (size exclusion chromatography), and $M_n$ (number average molecular weight) is generally determined by means of GPC-SEC.

The molecular weights of the polymers can, if appropriate, be set to the desired values by means of the regulators customary in trioxane polymerization and also by means of the reaction temperature and residence time. As regulators, it is possible to use acetals or formals of monohydric alcohols, the alcohols themselves and the small amounts of water which function as chain transfer agents and whose presence can in general never be avoided completely. The regulators are used in amounts of from 10 to 10 000 ppm, preferably from 20 to 5000 ppm.

As initiators (also referred to as catalysts), use is made of the cationic initiators customary in trioxane polymerization. Suitable initiators are protic acids such as fluorinated or chlorinated alkylsulfonic and arylsulfonic acids, e.g. perchloric acid, trifluoromethanesulfonic acid, or Lewis acids such as tin tetrachloride, arsenic pentafluoride, phosphorus pentafluoride and boron trifluoride and also their complexes and salt-like compounds, e.g. boron trifluoride etherates and triphenylmethyl hexafluorophosphate. The initiators (catalysts) are used in amounts of from about 0.01 to 1000 ppm, preferably from 0.01 to 500 ppm and in particular from 0.01 to 200 ppm. In general, it is advisable to add the initiator in diluted form, preferably in concentrations of from 0.005 to 5% by weight. As solvents for this purpose, it is possible to use inert compounds such as aliphatic, cycloaliphatic hydrocarbons, e.g. cyclohexane, halogenated aliphatic hydrocarbons, glycol ethers, etc. Particularly preferred solvents are triglyme (triethylene glycol dimethyl ether) and 1,4-dioxane.

In addition to the initiators, it is possible to make concomitant use of cocatalysts. These are alcohols of any type, for example aliphatic alcohols having from 2 to 20 carbon atoms, e.g. t-amyl alcohol, methanol, ethanol, propanol, butanol, pentanol, hexanol; aromatic alcohols having from 2 to 30 carbon atoms, e.g. hydroquinone; halogenated alcohols having from 2 to 20 carbon atoms, e.g. hexafluoroisopropanol; very particular preference is given to glycols of any type, in particular diethylene glycol and triethylene glycol; and aliphatic dihydroxy compounds, in particular diols having from 2 to 6 carbon atoms, e.g. 1,2-ethanediol, 1,3-propanediol, 1,4-butanediol, 1,6-hexanediol, 1,4-hexanediol, 1,4-cyclohexanediol, 1,4-cyclohexanedimethanol and neopentyl glycol.

Monomers, initiators, cocatalyst and, if appropriate, regulators can be premixed in any way or be introduced separately from one another into the polymerization reactor.

Furthermore, the components can comprise sterically hindered phenols to stabilize them, as described in EP-A 129369 or EP-A 128739.

The polymerization mixture is preferably deactivated immediately after the polymerization, preferably without a phase change occurring. The initiator residues (catalyst residues) are generally deactivated by addition of deactivators (termination agents) to the polymerization melt. Suitable deactivators are, for example, ammonia and primary, secondary or tertiary, aliphatic and aromatic amines, e.g. trialkylamines such as triethylamine, or triacetonediamine. Further suitable deactivators are salts having a basic reaction, e.g. sodium carbonate and borax, also the carbonates and hydroxides of the alkali metals and alkaline earth metals, and in addition also alkoxides such as sodium ethoxide. The deactivators are usually added in amounts of preferably from 0.01 ppmw (parts per million by weight) to 2% by weight to the polymers. Furthermore, alkali metal and alkaline earth metal alkyls having from 2 to 30 carbon atoms in the alkyl radical are preferred as deactivators. Particularly preferred metals are Li, Mg and Na, with n-butyllithium being particularly preferred.

POMs from trioxane are generally obtained by bulk polymerization, for which purpose any reactors having a good mixing action can be used. The reaction can be carried out homogeneously, e.g. in a melt, or heterogeneously, e.g. as polymerization to form a solid or solid granules. Examples of suitable reactors are pan reactors, plowshare mixers, tube reactors, List reactors, kneaders (e.g. Buss kneaders), extruders having, for example, one or two screws and stirred reactors. The reactors can have static or dynamic mixers.

In a bulk polymerization, e.g. in an extruder, a melt seal is formed by the molten polymer, as a result of which volatile constituents remain in the extruder. The above monomers are metered into the polymer melt present in the extruder, either together with or separately from the initiators (catalysts), at a preferred temperature of the reaction mixture of from 62 to 114° C. The monomers (trioxane) are preferably also metered in in the molten state, e.g. at from 60 to 120° C. Owing to the exothermic nature of the process, it is usually only necessary to melt the polymer in the extruder at the beginning of the process; subsequently, the quantity of heat liberated is sufficient to melt the POM polymer formed and keep it molten.

The melt polymerization is generally carried out at from 1.5 to 500 bar and from 130 to 300° C., and the residence time of the polymer mixture in the reactor is usually from 0.1 to 20 minutes, preferably from 0.4 to 5 minutes. The polymerization is preferably continued to a conversion above 30%, e.g. from 60 to 90%.

In all cases, a crude POM which as mentioned comprises considerable amounts, for example up to 40%, of unreacted residual monomers, in particular trioxane and formaldehyde, is obtained. Formaldehyde can be present in the crude POM even if only trioxane has been used as monomer, since it can be formed as degradation product of trioxane. In addition, other oligomers of formaldehyde, e.g. the tetramer tetroxane, can also be present.

This crude POM is degassed in one or more stages in known degassing apparatuses, for example in degassing pots (flash pots), degassing extruders having one or more screws, thin film evaporators, spray dryers or other customary degassing apparatuses. Particular preference is given to degassing pots (flash pots).

A preferred mode of operation for the degassing of the crude POM is to carry out degassing in a first flash pot to less than 6 absolute bar so as to give a gaseous stream and a liquid stream which is fed to a second flash pot which is operated at less than 2 bar absolute to give a vapor stream which is recycled to the monomer plant.

For example, in a two-stage degassing process, the pressure in the first stage can preferably be from 2 to 18 bar, in particular from 2 to 15 bar and particularly preferably from 2 to 10 bar, and that in the second stage can preferably be from 1.05 to 4 bar, in particular from 1.05 to 3.05 bar and particularly preferably from 1.05 to 3 bar.

Residual monomers liberated during degassing are, if appropriate, taken off as one or more vapor streams and passed to a condenser. The condenser is preferably operated so that the condensate stream obtained has a higher trioxane content than the uncondensed vapor stream.

This gives a condensate which is recycled to the polymerization reactor and a gaseous, formaldehyde-comprising stream. The partially degassed polyoxymethylene homopolymer or copolymer is subsequently fed to an extruder or kneader and provided therein with customary additives and processing aids (referred to collectively as additives) in the amounts customary for these materials. Such additives are, for example, lubricants or mold release agents, colorants such as pigments or dyes, flame retardants, antioxidants, stabilizers against the action of light, formaldehyde scavengers, polyamides, nucleating agents, fibrous and pulverulent fillers or reinforcing materials or antistatics and also other additives or mixtures thereof.

The desired POM product is obtained as a melt from the extruder or kneader.

At the dome of the extruder or kneader, a further formaldehyde-comprising secondary stream is taken off as extruder or kneader offgas.

All formaldehyde-comprising secondary streams obtained in the production plant C are recirculated directly, i.e. in the form in which they are obtained in the production plant C without chemical changes and without addition of auxiliaries, in particular without addition of water, to a suitable point in the trioxane production plant B.

Both the chemical composition and the energy content of these are utilized in the overall process for the preparation of POM.

The gaseous, formaldehyde-comprising secondary streams which are obtained in the single-stage or multistage depressurization of the polymer melt from the polymerization reactor and remain in the gaseous state after the condensation are, according to the invention, recycled to the production plant C.

The gaseous formaldehyde-comprising stream from the production plant C is preferably recycled to the first column of the production plant B.

Here, the operating conditions in the condenser are preferably set so that the proportion of trioxane in the gaseous formaldehyde-comprising stream from the production plant C which is recycled to the production plant B is less than 80% by weight, preferably less than 60% by weight, particularly preferably less than 40% by weight.

This stream generally has a formaldehyde content of preferably at least 25% by weight, more preferably at least 50% by weight.

One or more further formaldehyde-comprising secondary streams, viz. the extruder or kneader offgas, are obtained at the dome of the extruder or kneader and these are, according to the invention, likewise recycled directly, i.e. without chemical or physical changes, to the production plant B.

A subatmospheric pressure is generally generated at the dome of the extruder or kneader, frequently in the range below 800 mbar in a first stage and under lower pressure, frequently in the range below 500 mbar, in a second stage.

The extruder or kneader offgas is, according to the invention, taken up in the liquid ring pump which is already present in the production plant B to compress a water-rich liquid stream, in particular the overhead stream from the evaporation of the formaldehyde feed stream from a starting concentration of from about 10 to 60% by weight, in particular from about 15 to 45% by weight, located upstream of the reactor for the preparation of trioxane to the pressure of the fourth column, in order to remove water.

In particular, the extruder offgas taken up in the liquid ring pump is compressed to a pressure of from 2 to 7 bar absolute, preferably to about 5 bar absolute.

The invention is illustrated below with the aid of a drawing and examples.

The process of the invention enables at least 90% of methanol, methylal, methyl formate and other methanol derivatives from the low boiler stream to be used as starting material for the preparation of formaldehyde in the first production plant.

Figure 2:
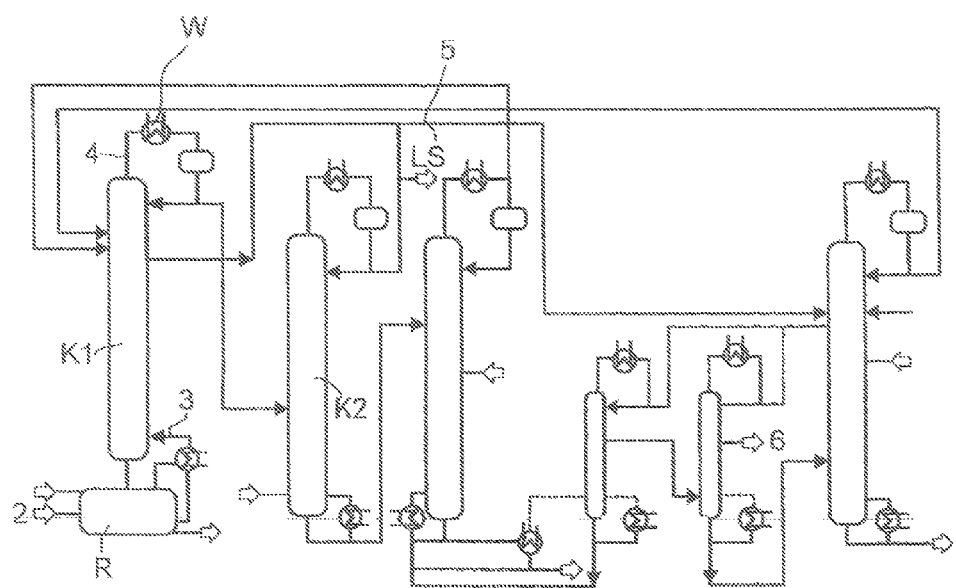

In the drawing:

FIG. 1 shows a flow diagram of the coupled operation according to the invention of a formaldehyde plant, a trioxane plant and a polyoxymethylene homopolymer or copolymer plant, FIG. 2 shows a preferred embodiment of a trioxane production plant.

The flow diagram in FIG. 1 schematically shows a first production plant A (formaldehyde production plant), a second production plant B (trioxane production plant) and a third production plant C (polyoxymethylene homopolymer or copolymer plant).

A methanol stream 1 is fed to the first production plant A and an aqueous formaldehyde-comprising stream 2 is taken off therefrom and fed to the second production plant B. A low boiler stream 5 is taken off from this and is recycled to the first production plant A.

A pure trioxane stream 6 is obtained from the second production plant B and is fed to the third production plant C for the preparation of polyoxymethylene homopolymers or copolymers. Polyoxymethylene homopolymers or copolymers 7 are taken off from the third production plant C.

A recycle stream having no further designation from the third production plant C to the second production plant B illustrates the coupling in terms of material of these two production plants.

FIG. 2 shows a preferred embodiment of a second production plant B:

An aqueous formaldehyde-comprising stream 2 is fed together with an acid catalyst to the second reactor and is trimerized therein to trioxane. A trioxane/formaldehyde/water mixture 3 is taken off from the reactor R and is fractionally distilled in a first column K1 to give crude trioxane as overhead stream 4. The overhead stream 4 is condensed in a condenser W at the top of the column. Part of the condensate is returned as runback to the column K1 and the remainder is, in the preferred embodiment depicted in the figure, fed to a low boiler removal column K2. A stream 5 comprising low boilers is taken off from the low boiler removal column K2 and is, according to the invention, recycled to the first production plant A, which is not shown in FIG. 2.

The bottom stream from the low boiler removal column K2 is purified in further distillation stages which are not described in more detail to give pure trioxane, stream 6. Pure trioxane, stream 6, is fed as feed stream to the third production plant C, which is not shown in FIG. 2, for the preparation of polyoxymethylene homopolymers or copolymers.

The invention claimed is:

1. A process for preparing polyoxymethylene homopolymers or copolymers (7) by homopolymerization or copolymerization of trioxane, starting from methanol (1), in which
    methanol (1) is oxidized in a first reactor in a first production plant (A) to give an aqueous formaldehyde-comprising stream (2) which
    is fed to a second production plant (B) in which
        the formaldehyde is trimerized in the presence of an acid catalyst in a second reactor (R) to form trioxane and from which a trioxane/formaldehyde/water mixture (3) is taken off,
        the trioxane/formaldehyde/water mixture (3) is fractionally distilled in a first column (K1) to give crude trioxane as overhead stream (4)
        and the overhead stream (4) is condensed in a condenser (W) at the top of the column to give a condensate, a substream (4a) of the condensate is returned to the first column (K1) and the remaining substream (4b) is passed to further work-up in one or more further process stages to give pure trioxane (6), with one of these further process stages comprising removal of low boilers (5) selected from the group consisting of methyl formate, methylal, bis(methoxymethyl) ether and methanol by distillation in a low boiler removal column (K2), and
    the pure trioxane (6) is fed to a third production plant (C) in which it is homopolymerized or copolymerized to form polyoxymethylene homopolymers or copolymers (7), wherein the low boiler stream (5) from the low boiler removal column (K2) is recycled to the feed stream into the first reactor in the first production plant (A), wherein the low boiler stream has the following main components: methanol up to 50% by weight, methyl formate up to 40% by weight, methylal up to 30% by weight and trioxane less than 10% by weight.

2. The process according to claim 1, wherein a crude polyoxymethylene homopolymer or copolymer which still comprises residual monomers is prepared in the third production plant (C) and is degassed in one or more stages to give one or more vapor streams which are optionally fed to a condenser to give a condensate which is recycled to the polymerization reactor and a gaseous, formaldehyde-comprising stream, and also a partially degassed polyoxymethylene homopolymer or copolymer which
    is fed to an extruder or kneader and mixed therein with customary additives and processing aids to give a polymer melt and a formaldehyde-comprising extruder or kneader offgas is taken off from the extruder or kneader, with all formaldehyde-comprising secondary streams from the production plant (B) being recycled directly without addition of auxiliaries to the production plant (C).

* * * * *